United States Patent [19]

Zoeller et al.

[11] Patent Number: 5,097,069

[45] Date of Patent: Mar. 17, 1992

[54] PROCESS FOR DECOMPOSING α,β-UNSATURATED CARBONYL COMPOUNDS IN REFINING ACETIC ANHYDRIDE AND/OR ACETIC ACID

[75] Inventors: Joseph R. Zoeller; Charles E. Outlaw; Regina M. Moncier, all of Kingsport, Tenn.

[73] Assignee: Eastman Kodak Company, Rochester, N.Y.

[21] Appl. No.: 681,271

[22] Filed: Apr. 8, 1991

[51] Int. Cl.$^5$ .............................................. C07C 51/54
[52] U.S. Cl. ..................................... 562/898; 562/891
[58] Field of Search ............................... 562/898, 891

[56] References Cited

U.S. PATENT DOCUMENTS 4,442,304  4/1984  Erpenbach et al. ................. 562/898
4,792,420  12/1988  Kizkalla ............................. 562/898

FOREIGN PATENT DOCUMENTS 124908  5/1946  Australia ............................ 562/898

*Primary Examiner*—Jose G. Dees
*Assistant Examiner*—Keith MacMillan
*Attorney, Agent, or Firm*—J. Frederick Thomsen; William P. Heath, Jr.

[57] ABSTRACT

Unsaturated ketones such as mesityl oxide may be removed from acetic anhydride, or mixtures of acetic anhydride and acetic acid, by heating a solution comprising (1) acetic anhydride, or a mixture of acetic anhydride and acetic acid, (2) an α,β-unsaturated ketone, (3) ferrous (Fe II) and/or cobaltous (Co II) ion, (4) a cation selected from alkali metals, alkaline earth metals, quaternary organoammonium, quaternary organophosphonium and mixtures thereof, and (5) iodide ion.

5 Claims, No Drawings

PROCESS FOR DECOMPOSING α,β-UNSATURATED CARBONYL COMPOUNDS IN REFINING ACETIC ANHYDRIDE AND/OR ACETIC ACID

This invention pertains to the purification of acetic anhydride and mixtures comprising acetic anhydride and acetic acid. More specifically, this invention pertains to a purification process wherein the concentration of α,β-unsaturated compounds present in acetic anhydride, acetic acid or, especially, mixtures thereof is reduced.

The preparation of acetic anhydride by contacting a mixture comprising methyl iodide and methyl acetate and/or dimethyl ether with carbon monoxide in the presence of a rhodium catalyst has been reported extensively in the patent literature. See, for example, U.S. Pat. Nos. 3,927,078; 4,046,807; 4,115,444; 4,374,070; 4,430,273; and 4,559,183 and European Patents 8396; 87,869; and 87,870. These patents disclose that the reaction rate can be increased if the catalyst system includes a promoter such as certain amines and quaternary ammonium compounds, phosphines and phosphonium compounds and inorganic compounds such as lithium compounds. The crude or partially-refined product obtained from such acetic anhydride processes typically comprises a mixture of acetic anhydride and acetic acid as a result of the use of acetic acid as a process solvent and/or the coproduction of acetic acid by including methanol and/or water in the feed to the carbonylation reactor.

The acetic anhydride and acetic acid obtained from the carbonylation processes referred to above must be purified and refined to meet the purity requirements of users thereof. One of the most important purity specifications which is especially difficult to achieve is the concentration of "reducing substances". See, for example, Published European Patent Application 372,993. Typical specifications require a permanganate reducing substances test value (permanganate time) of at least 30 minutes according to a modification of the Substances Reducing Permanganate Test, American Chemical Society Specifications published in Reagent Chemicals, 6th Ed., American Chemical Society, Washington, D.C., pp. 66 and 68.

It is known (U.S. Pat. Nos. 4,252,748; 4,444,624; and 4,717,454) that acetone is formed during the manufacture of acetic anhydride by continuous carbonylation processes. Typically, the acetone formed accumulates in the carbonylation reactor of the acetic anhydride production system to a maximum level of about 4.0 to 8.0 weight percent, based on the total weight of the contents of the carbonylation reactor. It is believed that acetone is consumed in the reactor to produce process "tars" and other undesirable by-products of the carbonylation process. Removal of acetone is not essential to the operation of the production system and the cost of its separation and purification is not justified by the value of the relatively small amount of acetone formed.

We have found that mesityl oxide (4-methyl 3-buten-2-one) is the primary component of the undesirable reducing substances formed during the continuous operation of the carbonylation processes described in prior art cited above. It is believed that mesityl oxide is formed from acetone according to the reaction:

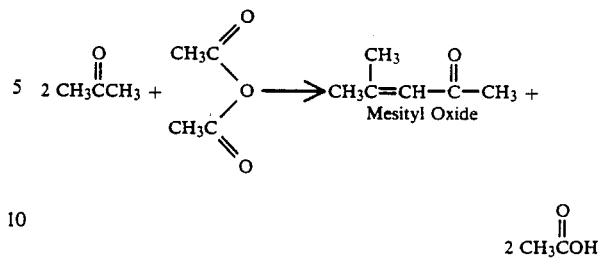

Mesityl oxide is extremely difficult to separate from mixtures of acetic acid and acetic anhydride by conventional, industrial distillation equipment since its boiling point (130° C.) is midway between the boiling points of acetic acid (118° C.), and acetic anhydride (140° C.).

We also have observed the presence of 2,4-pentanedione (acetylacetone) in the carbonylation reactor. This compound also may retard reaction rates, possibly by the formation of another α,β-unsaturated ketone from the acetylation of its enol isomer, e.g.:

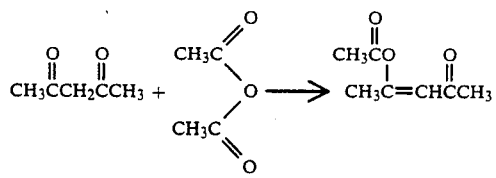

or by direct coordination via the enolate anion. The above α, β-unsaturated ketone (4 acetoxy-3 buten-2-one) also may retard the carbonylation rate.

We have discovered that the concentration of α,β-unsaturated ketones, e.g., mesityl oxide, including compounds capable of generating α,β-unsaturated ketones, e.g., 2,4-pentanedione, present in acetic anhydride, or mixtures of acetic anhydride and acetic acid, can be reduced substantially by heating a solution comprising (1) acetic anhydride, or a mixture of acetic anhydride and acetic acid, (2) an α,β-unsaturated ketone, (3) ferrous (Fe II) and/or cobaltous (Co II) ion, (4) a cation selected from alkali metals, alkaline earth metals, quaternary organoammonium, quaternary organophosphonium and mixtures thereof, and (5) iodide ion. Although the solution may be heated to temperatures as high as 250° C., maintaining the solution at about 75° to 175° C. for a period of time in the range of about 10 to 300 minutes will result in the decomposition of approximately 50 to 100% of the undesirable α,β-unsaturated ketone. Preferably, the heating is at a temperature in the range of about 100° to 150° C. for a period of about 60 to 200 minutes. The amount of the α,β-unsaturated ketone(s) present in the acetic anhydride, acetic acid or mixture thereof, which is treated in accordance with our invention, may be as high as 2000 ppm but usually is in the range of about 25 to 400 ppm. The acetic anhydride/acetic acid mixtures which may be treated according to our invention may contain up to about 80 weight percent acetic acid, based on the total weight of acetic anhydride and acetic acid.

The concentrations of solution components (3), (4) and (5) can vary substantially depending, for example, on the time and temperature at which the mixture is heated, and the particular component, especially component (4), employed, the concentration of the α,β-unsaturated ketone(s), and the degree of α,β- unsaturated ketone(s) decomposition desired. The upper limits of the components are limited only by practical considerations and/or the solubility of each component in acetic anhydride or acetic anhydride/acetic acid mixture. The particular materials employed as components (3), (4) and (5), the amounts thereof and the compounds from which they are derived may be readily determined by those skilled in the art without undue experimentation.

The amount of ferrous and/or cobaltous ion usually should be at least 50 ppm, based on the total weight of the solution, i.e., components (1)–(5). The maximum concentration which may be used depends on the particular material being treated since ferrous and cobaltous compounds, in general, are significantly more soluble in acetic acid than they are in acetic anhydride. Normally, the concentration of ferrous and/or cobaltous ion is at least 50 ppm with a possible maximum concentration of about 1000 ppm. The preferred concentration of ferrous and/or cobaltous ion, is about 150 to 600 ppm. Ferrous ion is preferred.

The cation constituting component (4) may be selected from a wide variety of inorganic cations, e.g., alkali metal and alkaline earth metal cations, and organoammonium or organophosphonium cation. The quaternary organoammonium and quaternary organophosphonium cations are tetra substituted nitrogen and phosphorus ions which may contain up to about 24 carbon atoms. The quaternary ammonium cations may be selected from heterocyclic aromatic residues in which at least one ring hetero atom is a quaternary nitrogen atom. Examples of such quaternary organoammonium and quaternary organophosphonium cations include tetra (hydrocarbyl)phosphonium such as tributyl(methyl)phosphonium, tetrabutylphosphonium, tetraoctylphosphonium, triphenyl(methyl)phosphonium, tetraphenylphosphonium, and the like; tetra(hydrocarbyl)ammonium such as tetrabutylammonium and tributyl(methyl)ammonium; and heterocyclic aromatic residues such as N-methylpyridinium, N,N'-dimethylimidazolium, N-methyl-3-picolinium, N-methyl-2,4 lutidinium, N-methyl-2,4-lutidinium and N-methylquinolinium. The preferred quaternary organoammonium and quaternary organophosphonium cations comprise tetraalkylphosphonium, triphenyl(alkyl)phosphonium, tetraalkylammonium, and N,N'-dialkylimidazolium wherein the alkyl groups contain up to about 8 carbon atoms. Component (4) preferably is magnesium or, especially, lithium.

The concentration of the cation component (4) may vary substantially depending on the particular cation employed. For example, the amount of cation used may be in the range of from about 0.5 to 50.0 moles cation per mole of ferrous and/or cobaltous ion. Cation (4) preferably is used in amounts which give a cation (4) to ferrous and/or cobaltous ion mole ratio of about 1.0 to 20.0. Typical concentrations of iodide ion are 400 ppm to 4.0 weight percent with the preferred range being about 2000 ppm to 3.0 weight percent.

The purification process of the present invention may be carried out as a batch or continuous operation. The pressure at which the process is practiced is not critical and thus pressures over the range of 20 torr to 100 bar may be used. In a preferred embodiment, the purification process is operated in conjunction with known continuous processes for the production of acetic anhydride, or the coproduction of acetic anhydride and acetic acid, by carbonylation chemistry. Typically, in such processes, an effluent is continuously removed from the carbonylation reactor and separated into a major fraction comprising methyl iodide, methyl acetate and/or dimethyl ether, acetic acid and acetic anhydride and a minor fraction comprising a solution of catalyst components and a ferrous and/or cobaltous compound in a mixture of acetic acid and acetic anhydride. The minor fraction is recycled to the carbonylation zone and the major fraction is separated by a series of distillations into its component parts. Components (3), (4) and (5) may be added, e.g., as a solution in acetic acid, to one of the distillation columns by adding them to the column feed, to a column reboiler vessel or directly to the column.

Our novel process involving the decomposition of $\alpha,\beta$-unsaturated ketones is further illustrated by the following examples.

EXAMPLES 1-14 AND COMPARATIVE EXAMPLES 1-14

In Comparative Example 1, a mixture of 50 g acetic anhydride and 50 g acetic acid to which mesityl oxide is added is heated at reflux for 3 hours. In Examples 1–7, the procedure is repeated except that (i) ferrous or cobaltous ion, (ii) a cation selected from alkali metals, alkaline earth metals, quaternary organoammonium, quaternary organophosphonium and mixtures thereof, and (iii) iodide ion are added to the mesityl oxide-containing mixture of acetic anhydride and acetic acid prior to refluxing for 3 hours. In Comparative Examples 2–14, the procedure of Comparative Example 1 is repeated except that one of the 3 essential components is not added and/or is replaced with another material. The additional compounds and the amounts thereof used in these examples are:

Example 1 0.275 g ferrous iodide; 1.480 g lithium acetate dihydrate

Example 2 0.157 g cobaltous acetate tetrahydrate; 0.238 g lithium iodide

Example 3 0.154 g ferrous acetate; 3.360 g N,N'-dimethylimidazolium iodide

Example 4 0.154 g ferrous acetate; 5.400 g tetrabutylammonium iodide

Example 5 0.154 g ferrous acetate; 5.860 g triphenyl(methyl)phosphonium iodide

Example 6 0.154 g ferrous acetate; 5.790 g tetrabutylphosphonium iodide

Example 7 0.275 g ferrous iodide; 0.190 g magnesium acetate

Comparative 0.157 g nickelous iodide; Example 2 1.480 g lithium acetate dihydrate Comparative 0.271 g chromium (II) iodide; Example 3 1.480 g lithium acetate dihydrate Comparative 0.238 g lithium iodide; Example 4 0.190 g magnesium acetate Comparative 0.157 g cobalt (II) acetate tetrahydrate; Example 5 0.080 g lithium bromide Comparative 0.275 g ferrous iodide Example 6

Comparative 0.154 g ferrous acetate Example 7

Comparative 0.154 g ferrous acetate; Example 8 1.480 g lithium acetate dihydrate Comparative 1.480 g lithium acetate dihydrate Example 9

Comparative 0.238 g lithium iodide Example 10

Comparative 3.360 g N,N'-dimethylimidazolium Example 11 iodide

Comparative 5.400 g tetrabutylammonium iodide Example 12

Comparative Example 13  5.860 g triphenyl(methyl)phosphonium iodide
Comparative Example 14  5.790 g tetrabutylphosphonium iodide Each of the mixtures of the above examples is analyzed before and after the 3-hour reflux period. The mesityl oxide concentration (in ppm) of each mixture prior to heating (Initial) and after heating (Final) and the weight percent of mesityl oxide depleted from each mixture are shown in Table I wherein "C" refers to a comparative example, e.g. C-1 is comparative Example 1.

TABLE I

| Example | Mesityl Oxide Conc. Initial | Mesityl Oxide Conc. Final | Mesityl Oxide Depleted |
|---------|---------|-------|------|
| C-1 | 294 | 266 | 10% |
| 1 | 368 | 0 | 100% |
| 2 | 323 | 32 | 90% |
| 3 | 264 | 48 | 82% |
| 4 | 340 | 175 | 49% |
| 5 | 299 | 98 | 63% |
| 6 | 272 | 137 | 50% |
| 7 | 353 | 0 | 100% |
| C-2 | 378 | 196 | 48% |
| C-3 | 375 | 300 | 20% |
| C-4 | 321 | 296 | 8% |
| C-5 | 330 | 304 | 8% |
| C-6 | 304 | 184 | 39% |
| C-7 | 306 | 185 | 40% |
| C-8 | 317 | 201 | 37% |
| C-9 | 348 | 320 | 8% |
| C-10 | 304 | 284 | 7% |
| C-11 | 245 | 245 | 0% |
| C-12 | 314 | 314 | 0% |
| C-13 | 274 | 254 | 7% |
| C-14 | 286 | 256 | 10% |

Examples 1-7 demonstrate the capability of a combination of (i) ferrous or cobaltous ion, (ii) a cation selected from alkali metals, alkaline earth metals, quaternary organoammonium, quaternary organophosphonium and mixtures thereof, and (iii) iodide ion to deplete mesityl oxide from mixtures of acetic anhydride and acetic acid. Comparative Examples 2 and 3 show that other transition metal salts (nickel acetate and chromium acetate) are substantially less effective in depleting mesityl oxide. Reference Examples 4-14 show that the omission of any of the 3 components required for depletion or decomposition of the $\alpha,\beta$-unsaturated ketone gives inferior results.

EXAMPLE 8

To a solution of 50 g acetic acid and 50 g acetic anhydride containing 367 ppm mesityl oxide and 60 ppm 2,4-pentanedione is added 0.154 g ferrous acetate and 0.238 g lithium iodide. The resulting solution is heated at reflux for 3 hours and then analyzed for mesityl oxide and 2,4-pentanedione. The presence of neither mesityl oxide nor 2,4-pentanedione is detected.

The invention has been described in detail with particular reference to preferred embodiments thereof, but it will be understood that variations and modifications can be effected within the spirit and scope of the invention.

We claim:

1. Process for reducing the concentration of an $\alpha,\beta$-unsaturated ketone present in acetic anhydride or a mixture of acetic anhydride and acetic acid which comprises heating at a temperature of about 75 to 175° C. a solution comprising (1) acetic anhydride, or a mixture of acetic anhydride and acetic acid, (2) an $\alpha,\beta$-unsaturated ketone, (3) ferrous (Fe II) and/or cobaltous (Co II) ion, (4) a cation selected from alkali metals, alkaline earth metals, quaternary organoammonium, quaternary organophosphonium and mixtures thereof, and (5) iodide ion.

2. Process according to claim 1 wherein the heating is at about 100 to 150° C; component (3) is present in a concentration of about 150 to 600 ppm; component (4) is present in an amount of about 0.5 to 50.0 moles cation per mole of ferrous and/or cobaltous ion; and component (5) is present in a concentration of about 2000 ppm to 3 weight 3. Process for reducing the concentration of mesityl oxide present in acetic anhydride or a mixture of acetic anhydride and acetic acid which comprises heating at a temperature of about 75° to 175° C. a solution comprising (1) acetic anhydride, or a mixture of acetic anhydride and acetic acid, (2) mesityl oxide (3) ferrous (Fe II) ion, (4) a cation selected from alkali metals, alkaline earth metals, quaternary organoammonium, quaternary organophosphonium and mixtures thereof, and (5) iodide ion.

4. Process according to claim 3 wherein the heating is at about 100° to 150° C.; component (3) is present in a concentration of about 150 to 600 ppm; component (4) is present in an amount of about 0.5 to 50.0 moles cation per mole of ferrous ion; and component (5) is present in a concentration of about 2000 ppm to 3 weight percent.

5. Process for reducing the concentration of mesityl oxide present in acetic anhydride or a mixture of acetic anhydride and acetic acid which comprises heating at about 100 ° to 150° C. a solution comprising (1) acetic anhydride, or a mixture of acetic anhydride and acetic acid, (2) mesityl oxide (3) ferrous (Fe II) ion, (4) a cation selected from alkali metals, alkaline earth metals, quaternary organoammonium, quaternary organophosphonium and mixtures thereon, and (5) iodide ion; wherein component (3) is present in a concentration of about 150 to 600 ppm; component (4) is present in an amount of about 1 to 20 moles cation per mole of ferrous ion; and component (5) is present in a concentration of about 2000 ppm to 3 weight percent.

* * * * *